United States Patent [19]

Arribas et al.

[11] Patent Number: 5,354,432
[45] Date of Patent: Oct. 11, 1994

[54] PROCESS FOR THE PRODUCTION OF ISOCYANATES AND FOR WORKING UP THE RESIDUE

[75] Inventors: Javier C. Arribas, Cambrils; Ciriaco D. Arribas, La Granja; Salvador V. Rodriguez, Tarragona, all of Spain

[73] Assignee: Bayer Aktiengesellschaft, Leverkusen, Fed. Rep. of Germany

[21] Appl. No.: 991,011

[22] Filed: Dec. 15, 1992

[30] Foreign Application Priority Data

Dec. 23, 1991 [DE] Fed. Rep. of Germany ....... 4142769

[51] Int. Cl.$^5$ .............................................. B01D 3/34
[52] U.S. Cl. .................................... 203/68; 203/70; 203/73; 203/DIG. 25; 560/352; 528/502; 528/902
[58] Field of Search ............... 203/68, 70, 71, 73, 203/DIG. 25; 560/352, 347; 528/497, 498, 502, 503, 902; 525/452

[56] References Cited

U.S. PATENT DOCUMENTS

| | | | |
|---|---|---|---|
| 2,889,257 | 6/1959 | Griffin et al. | 202/52 |
| 3,658,656 | 4/1972 | Adica et al. | 203/68 |
| 3,729,386 | 4/1973 | Irwin et al. | 203/68 |
| 3,884,951 | 5/1975 | Oswald | 560/357 |
| 3,892,634 | 7/1975 | Hajek et al. | 203/89 |
| 3,897,314 | 7/1975 | Diebsch et al. | 203/89 |
| 3,912,600 | 10/1975 | Hatfield, Jr. et al. | 203/88 |
| 4,065,362 | 12/1977 | Kataoka et al. | 203/59 |
| 4,289,589 | 9/1981 | Koehler et al. | 203/49 |
| 4,297,456 | 10/1981 | Reischl et al. | 203/47 |

FOREIGN PATENT DOCUMENTS

| | | |
|---|---|---|
| 269218 | 6/1988 | European Pat. Off. . |
| 2246920 | 4/1973 | Fed. Rep. of Germany ........ 203/68 |
| 1353787 | 5/1974 | United Kingdom . |
| 1408745 | 10/1975 | United Kingdom . |
| 9009990 | 9/1990 | World Int. Prop. O. . |

OTHER PUBLICATIONS

Ullmanns Encyklopadie der technischen Chemie, rth Edition, vol. 13, pp. 347–357, Verlag Chemie CmbH, D-6940 Weinheim, 1977.

Primary Examiner—Virginia Manoharan
Attorney, Agent, or Firm—Joseph C. Gil; Lyndanne M. Whalen

[57] ABSTRACT

A process for the production of pure distilled isocyanates in which the corresponding amine is reacted with phosgene in a suitable solvent and working up of the isocyanate containing solution obtained by multistage distillation into pure isocyanate, pure solvent and a residue. The residue is then charged to a vessel containing at least one hydrocarbon having a high boiling point. The contents of this vessel are then heated with stirring to distill off any free isocyanate present. The remaining residue is a solid which may be disposed of readily.

5 Claims, 1 Drawing Sheet

PROCESS FOR THE PRODUCTION OF ISOCYANATES AND FOR WORKING UP THE RESIDUE

BACKGROUND OF THE INVENTION

This invention relates to a process for the production of pure distilled isocyanates by reaction of the corresponding amines with phosgene in a suitable solvent and working up of the reaction product by multistage distillation.

The industrial production of distilled isocyanates by reaction of amines with phosgene in solvents is known and is described in detail in the literature (Ullmanns Encyklopadie der technischen Chemie, 4th Edition, Vol. 13, pages 347–357, Verlag Chemie GmbH, D-6940 weinheim, 1977). This disclosure also teaches that a stream of secondary product is obtained in the course of the production of pure distilled isocyanates. This stream of secondary product has to be disposed of as residue after the removal of free isocyanates by distillation. It is possible on a laboratory scale to remove considerable amounts of more free isocyanate from this stream by distillation. However, the residue remaining becomes a hard crosslinked mass which can no longer be handled in the industrial process. On a commercial production scale, therefore, around 20 to 40% free isocyanate is left in the residue stream to be disposed of to ensure that this stream can be handled. This results in the loss of valuable material and more waste to be disposed of.

Processes for recovering more free isocyanate from the residue are known. For example, GB-PS 1,408,745 describes an extraction process for recovering the free isocyanate. EP 269,218 describes a working up process in which the residue stream is heated with a bath of molten metal or metal salts. DE 2,915,830 describes a process for distilling the stream of residue in a fluidized bed. Each one of these processes requires expensive apparatus and/or auxiliaries. Auxiliaries such as metals or metal salts seriously complicate the subsequent disposal process.

SUMMARY OF THE INVENTION

It is an object of the present invention to provide a technically simple and safe process for recovering free isocyanate from the distillation residues obtained during isocyanate production.

It is another object of the present invention to provide a process for recovering free isocyanate from the distillation residue of isocyanate production without loss of substantial amounts of the desired isocyanate and without the use of expensive apparatus and auxiliaries.

It is a further object of the present invention to provide an ecologically and economically desirable method for working up the residue of a reaction mixture containing free isocyanate which makes it possible to dispose of residue which can not be further distilled without polluting the environment.

These and other objects which will be apparent to those skilled in the art are accomplished by introducing the secondary stream from the isocyanate production process into a heated vessel in which a high boiling hydrocarbon that is inert under distillation conditions is present. The contents of the vessel are then distilled to recover the free isocyanate. The contents of the vessel are stirred during the introduction of the secondary stream and during the distillation to remove the free isocyanate. The residue remaining after the distillation is a solid which may be readily discharged from the vessel.

DETAILED DESCRIPTION OF THE INVENTION

Figure 1:
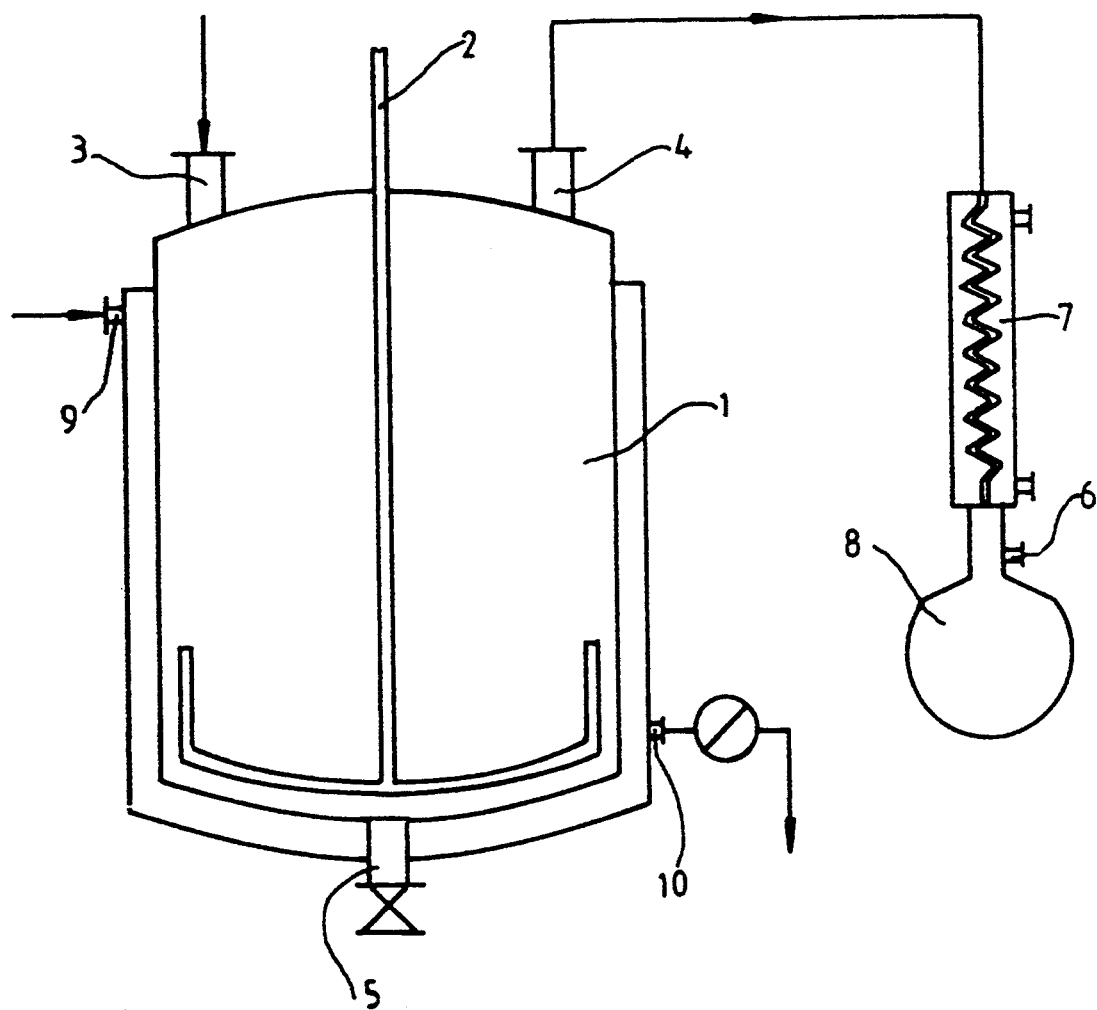
FIG. 1 illustrates the apparatus used in the processes described in the Examples.

The present invention relates to a process for the production of pure distilled isocyanates by reaction of the corresponding amines with phosgene in a suitable solvent and for working up the isocyanate solution obtained by multistage distillation. The isocyanate containing solution is distilled to separate it into three fractions: free pure isocyanate, pure solvent and a residue. The residue is then introduced into a stirred and heated vessel which is partly filled with a high-boiling hydrocarbon, preferably bitumen, which is inert under the distillation conditions. The free isocyanate still present in the residue is distilled off and the residue remaining is discharged as a free-flowing solid, cooled and burnt, optionally after grinding.

It is surprising that more isocyanate can be distilled off from the residue, depending on the isocyanate, in the presence of the high-boiling hydrocarbon or hydrocarbon mixtures, preferably bitumen, under the corresponding distillation conditions. A friable, free-flowing mass substantially free from free isocyanate is formed under the reaction conditions from the mixture of high-boiling hydrocarbon and the non-distillable polymer component of the residue. The residue is cooled before temporary storage or further processing.

The process of the present invention may be used to produce any of the known isocyanates and to work up the residues obtained in the production of any of the known isocyanates. It is particularly useful in the production of the following isocyanates: tolylene diisocyanate, 1,6-hexane diisocyanate, 1-isocyanato-3,3,5-trimethyl-5-isocyanatomethyl cyclohexane, 1,5-naphthylene diisocyanate, and diisocyanato-diphenyl methane by any of the known methods and in working up the isocyanate residues generated by such processes.

The residue obtained in the distillation-based working up phase of the production of isocyanates normally contains 20 to 80% by weight free isocyanate in addition to the polymeric secondary products and preferably 40 to 60% by weight free isocyanate.

A normal reactor with a heating jacket, which is suitable for high-pressure steam, may be used as the stirred reactor. Other heating media may of course also be used. In addition, the reactor should generally have a large vapor outlet for the isocyanate to be distilled off and also feed and auxiliary units. It is preferably fitted with a wall-sweeping stirrer of the type mentioned in the literature for highly viscous products. Anchor stirrers or helical stirrers are preferably used.

The reactor is operated at a temperature of 150° C. to 280° C. and preferably at a temperature of 180° to 230° C. under a pressure of 2 to 30 mbar and preferably under a pressure of 10 to 20 mbar. Distillation preferably takes place from a stirred sump vessel to which a suitable condensation system is connected. Before the beginning of distillation of the isocyanate containing residue, the reactor is first charged with a hydrocarbon or mixture of hydrocarbons in a quantity of 1 to 20% by volume and preferably in a quantity of 2 to 6% by volume, based on reactor volume. Suitable hydrocarbons are pure hydrocarbons or even technical mixtures, preferably bitumen, differing from the isocyanate with respect to boiling point at 15 mbar by at least 150° C. Asphalts and bitumen, of the type obtained as secondary products in oil refining, are particularly preferred, above all for economic reasons. Bitumens, of for example the B 80 and B 80 E type, of the B 300 type and the B 300 E type (according to DIN 52 010), are most particularly preferred.

On completion of distillation, the residue remaining may be introduced, for example, into a stirred water bath for cooling. When a mixture of isocyanate and solvent is recovered by the distillation, the mixture may be separated by any of the techniques known to those in the art (e.g., distillation).

The invention is illustrated by the following Examples.

EXAMPLES

Example 1

An apparatus of the type shown in FIG. 1 made up of a stirred tank 1 with a free-standing anchor stirrer 2 operated from above was used. The stirred tank had a height and a diameter of 50 cm (capacity 100 liters) and was provided with an inlet 3, a vapor outlet 4 and a bottom drainage pipe 5. It was designed to be heated with high pressure steam (30 bar) via a heating jacket with a steam inlet 9 and condensate outlet 10. The anchor stirrer 2 was of conventional design (distance from the walls and base of the tank 10 mm) and rotated at 7 revolutions per minute. The stirred tank 1 and anchor stirrer 2 were made of stainless steel. The stirred tank 1 was connected by the vapor outlet 4 to a laboratory vacuum pump via a water-cooled vapor condenser 7 and the gas outlet 6. The distillate accumulating was collected in the receiver vessel 8.

For the test, a residue consisting of 41% by weight 2,4-and 2,6-tolylene diisocyanate, 39% by weight polymeric residue and 20% by weight solvent was removed from the industrial production of tolylene diisocyanate (2,4-/2,6-isomer mixture containing 80% 2,4-tolylene diisocyanate).

6 kg bitumen of the B 80 type were introduced into the stirred tank 1 preheated with 30 bar steam. The tank was then evacuated to 15 mbar and heated to an internal temperature of 200° C. 7.5 kg/h of the residue described above (30 kg in all) were then run in with stirring over a period of 4 hours. The mixture was then distilled for 1 hour with no further addition. A dry, sand-like and free-flowing residue remained in the reactor and was drained off through the drainage pipe 5 with the stirrer running.

A mixture of 12.2 kg tolylene diisocyanate and 5.8 kg solvent was obtained in the distillation receiver 8. The reactor 1 contained 17.8 kg residue which no longer had any distillable tolylene diisocyanate.

EXAMPLE 2

The procedure was as in Example 1, except that 3.2 kg bitumen of the B 80 type were initially introduced and 7.5 kg per hour residue (60 kg in all) were run in over a period of 8 hours.

The properties of the residue obtained were comparable with those of Example 1.

A mixture of 24.5 kg tolylene diisocyanate and 11.7 kg solvent was obtained in the distillation receiver 8. 26.6 kg residue which no longer contained any distillable tolylene diisocyanate were obtained from the reactor 1.

EXAMPLE 3

A residue from the industrial production of 1,6-hexamethylene diisocyanate consisting of 44% by weight 1,6-hexa-methylene diisocyanate, 34% by weight residue and 22% by weight solvent was used for the test. 5 kg bitumen of the B 80 type were introduced into the reactor used in Example 1. The tank was evacuated to 12 mbar and then heated to an internal temperature of 190° C. 8 kg/h of the above-described residue (48 kg in all) were then run in with stirring over a period of 6 hours.

The mixture was then distilled for 90 minutes with no further addition. A dry, sand-like and free-flowing residue remained in the reactor and was drained off through the drainage pipe with the stirrer running.

A mixture of 17.5 kg 1,6-hexamethylene diisocyanate and 8.8 kg solvent was obtained in the distillation receiver 8. 21.4 kg residue which contained no more distillable 1,6-hexamethylene diisocyanate were obtained from the reactor 1.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:

1. A process for the production of isocyanates comprising
   a) reacting an amine with phosgene in the presence of a solvent,
   b) distilling the reaction product of a) to obtain isocyanate, solvent and a residue,
   c) introducing the residue from b) into a heated vessel in which a high boiling bitumen that is inert under the distillation conditions and has a boiling point at 15 mbar which is at least 150° C. higher than that of the isocyanate distilled off in b) is present with stirring,
   d) distilling isocyanate from the contents of the heated vessel used in c) and
   e) discharging solid residue from the vessel.

2. The process of claim 1 in which the solid residue of e) is free-flowing.

3. The process of claim 1 in which the solid residue of e) is ground.

4. The process of claim 3 in which the ground solid residue is cooled and incinerated.

5. The process of claim 1 in which the solid residue of e) is cooled and then incinerated.

* * * * *